United States Patent [19]

Bornengo et al.

[11] Patent Number: 4,816,608

[45] Date of Patent: * Mar. 28, 1989

[54] PROCESS FOR THE PREPARATION OF (2,2)-PARACYCLOPHANE AND DERIVATIVES THEREOF

[75] Inventors: Giorgio Bornengo, Novara; Alessandro Malacrida, Sovico; Stefano Campolmi, Novara; Maurizio A. Beretta, Milan, all of Italy

[73] Assignee: Montedison S.p.A., Milan, Italy

[*] Notice: The portion of the term of this patent subsequent to Jan. 3, 2006 has been disclaimed.

[21] Appl. No.: 66,508

[22] Filed: Jun. 26, 1987

[30] Foreign Application Priority Data

Jun. 27, 1986 [IT] Italy .................. 20939 A/86

[51] Int. Cl.$^4$ ................ C07C 25/00; C07C 25/18
[52] U.S. Cl. .................... 570/184; 570/199
[58] Field of Search .................. 570/183, 184, 199

[56] References Cited

U.S. PATENT DOCUMENTS

| | | | |
|---|---|---|---|
| 3,221,068 | 11/1965 | Gorham | 570/184 |
| 3,349,142 | 10/1967 | Yeh | 570/183 |
| 4,532,369 | 7/1985 | Hartner | 570/183 |

FOREIGN PATENT DOCUMENTS

| | | | |
|---|---|---|---|
| 704487 | 2/1965 | Canada | 570/129 |
| 807196 | 1/1959 | United Kingdom | 564/282 |

OTHER PUBLICATIONS

Reich et al., "J. Amer. Chem. Soc." vol. 91(13) Jun. 1969, pp. 3534-3543.

Reich et al., "J. Amer. Chem. Soc." vol. 91(13) Jun. 1969, pp. 3527-3532.

Primary Examiner—Werren B. Lone
Attorney, Agent, or Firm—Stevens, Davis, Miller & Mosher

[57] ABSTRACT

Process for the preparation of (2,2)-paracyclophane or derivatives thereof by the Hofmann elimination of p-methylbenzyl-trimethylammonium hydroxide or derivatives thereof, in an aqueous solution of an alkali metal hydroxide, wherein said elimination is carried out in the presence of a compound of the formula (I):

$$Y-A-(X)_n \qquad (I)$$

wherein A represents an aromatic group, Y an electron donor group, X an electron acceptor group, and n is an integer from 1 to 3.

17 Claims, No Drawings

PROCESS FOR THE PREPARATION OF (2,2)-PARACYCLOPHANE AND DERIVATIVES THEREOF

DESCRIPTION OF THE INVENTION

This invention relates to a process for the preparation of (2,2)-paracyclophane and derivatives thereof having the formula:

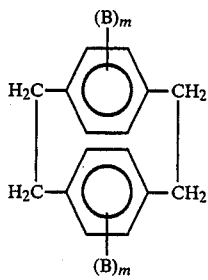

wherein B may be a halogen, an alkyl, an aralkyl, or a halogen-aralkyl radical containing up to 20 carbon atoms, and m is zero or an integer from 1 to 4.

More particularly, the invention relates to a process for preparing (2,2)-paracyclophane and its derivatives having the formula (II), starting from a p-methylbenzyletrimethylammonium hydroxide having the formula:

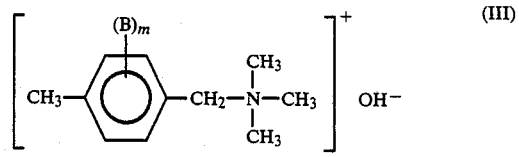

wherein B and m are the same as defined above, by the Hofmann elimination.

(2,2)-paracyclophane and its derivatives such as dichloro-(2,2)-paracyclophane, tetrachloro-(2,2)-paracyclophane, tetramethyl-(2,2)-paracyclophane, dimethyl-dichloro-(2,2)-paracyclophane, diethyl-(2,2)-paracyclophane, dibromo-(2,2)-paracyclophane, etc., are products well known in the literature and are generally utilized as intermediates in the preparation of the corresponding poly-p.xylylenes. Said polymers, and in particular poly-p.xylylene and its chlorinated derivatives, are advantageously utilized in the form of coating films in the field of the conformal coating, obtained by application according to the vacuum vapor deposition technique, in the electronic field.

Various processes have been proposed for preparing (2,2)-paracyclophane and its derivatives (II). However, such known processes are not fully satisfactory and are not suitable for being adopted on an industrial scale, mainly due to the low productivity of the process and to the difficulty in recovering the product from the reaction mixture.

Thus, for example, Organic Syntheses, Collective Vol. 5, John Wiley & Sons, Inc., New York/London, Sydney/Toronto, 1973, pages 883–886, describes a process for preparing (2,2)-paracyclophane by the Hofmann elimination starting from p-methylbenzyltrimethylammonium hydroxide obtained by reacting the corresponding bromide with silver oxide.

The elimination is carried out in the presence of an alkaline medium and an inert organic solvent (e.g., toluene) and a yield of about 10% is attained.

According to European patent application No. 108,297, it is possible to increase the reaction yield by carrying out the Hofmann elimination in an alkaline medium and in the presence of large amounts of dimethylsulphoxide. The large volumes and the long reaction times, generally exceeding 50 hours, lead to a low productivity in spite of high yields (about 70%). Furthermore, the recovery of dimethylsulphoxide and the unsatisfactory quality of the resulting product render this process little attractive for industrial scale utilization.

Generally, in all the known processes for producing (2,2)-paracyclophane, rather large amounts of poly-p.xylylene are formed, which in the presence of large amounts of organic solvent in the reaction medium, assumes a gelatine-like appearance and is difficult to be filtered off.

According to the present invention, it has now been discovered that (2,2)-paracyclophane and derivatives thereof having formula (II) may be prepared in a pure form, with high industrial yields, such as higher than 70% by mols, by carrying out the Hofmann elimination of p.-methylbenzyl-trimethylammonium hydroxide, optionally substituted in the nucleus, of formula (III) in an alkaline aqueous solution and in the presence of at least a catalytic amount of a compound having the formula:

wherein A represents an aromatic group, Y an electron donor group, X an electron acceptor group, and n is an integer from 1 to 3.

Preferably, A is a phenyl or naphthyl group; Y represents a group OR wherein R represents a hydrogen atom or an alkyl group containing from 1 to 4 carbon atoms; X represents a halogen atom, a nitro group, a nitrile group, a carboxyl, carbo-alkoxyl, carbonyl-alkyl or sulphonyl-alkyl group having from 1 to 6 carbon atoms in the alkyl part, or a sulphonic group; and n represents an integer from 1 to 3.

As said above, according to the present invention, the Hofmann elimination is carried in an aqueous reaction medium consisting or consisting essentially of an aqueous alkaline solution (sodium or potassium hydroxide) which is necessary for carrying out the substantially complete elimination, and, preferably, in the presence of an organic aprotic solvent.

As aprotic solvents, di-alkyl ethers of mono- and polyethylene glycols, dimethylsulphoxide (DMSO), dimethylformamide (DMF), and dimethylacetamide (DMA) have proved to be particularly suitable.

Di-alkyl ethers of mono- and poly-ethylene glycols having the formula (IV):

wherein $R_1$ and $R_2$, which may be the same or different, represent alkyl groups having from 1 to 5 carbon atoms, and p is an integer from 1 to 5, are preferred.

Examples of di-alkyl ethers of mono- and poly-ethylene glycols having formula (IV) which may be utilized in the process of the present invention are: di-ethylene-glycol-di-methyl ether, tetra-ethylene-glycol-di-methyl ether, di-ethylene-glycol-di-ethyl ether, diethyleneglycol-methyl-ethyl ether, pentaethylene-glycol-dimethyl ether, di-ethylene-glycol-di-propyl ether, etc.

Mixtures of di-alkyl ethers of formula (IV) may be also used.

The aromatic compound catalyst having formula (I) is a known compound, the preparation of which may be carried out by conventional synthesis methods. Among the catalysts within the above defined formula (I), p-nitrophenol, p-cyanophenol, p-chlorophenol, 4-nitro-alpha-naphthol, p-carbomethoxy-phenol, p-carboxyphenol, 2,4-dinitro-phenol, p-carboethoxy-phenol, p-hydroxy-acetophenone, p-hydroxy-benzene-sulphonic acid, alphanaphthol-4-sulphonic acid, etc., have proved to be particularly efficacious.

The p-methylbenzyltrimethylammonium hydroxide of formula (III), optionally substituted in the nucleus, may be prepared starting from the corresponding halide (chloride or bromide) by means of any conventional process. In practice, p-methylbenzyltrimethylammonium hydroxide, optionally substituted in the nucleus, is preferably formed in situ by the action of the alkali metal hydroxide present in the reaction medium. As an alternative, said hydroxide of formula (III) may be prepared separately by eluting an aqueous solution of the corresponding halide (chloride or bromide) through a basic ion exchange resin column.

The amount of the aprotic solvent or mixture thereof to be added in the reaction medium may vary over a wide range; weight ratios aprotic solvent/p-methylbenzyltrimethylammonium hydroxide, optionally substituted in the nucleus, of formula (III), of between 2 and 50, and preferably between 4 and 10, may be used.

As for the catalysts of formula (I), they are used in amounts which also may vary over a wide range, depending on the values taken by the other parameters, such as the temperature, reaction times, etc. However, excellent results are achieved by using molar amounts between 5% and about 30%, preferably between 10% and 20%, referred to p-methylbenzyltrimethylammonium hydroxide, optionally substituted in the nucleus, of formula (III).

According to this invention, the Hofmann elimination is carried out in an aqueous solution of an alkali metal hydroxide having a concentration higher than 10% by weight. As an alkali metal hydroxide, sodium or potassium hydroxide may be used. The concentration of the aqueous solution is preferably maintained during the Hofmann elimination reaction at a concentration between 15 and 35% by weight. Molar ratios of the alkali metal hydroxide to p-methylbenzyltrimethylammonium hydroxide (III) of between 1 and 10 are advantageously used.

The Hofmann elimination is carried out at a temperature between 50° and 150° C., preferably between 70° and 120° C., and for a time of 1 to 40 hours, and, preferably for 5 to 20 hours.

Inert organic solvents which are immiscible with water, such as, e.g., toluene, xylene, benzene, or tetraline, may be added to the reaction medium.

At the end of the elimination reaction, the resulting product is separated according to per se known and substantially conventional methods.

The process of this invention permits one to obtain, with industrially acceptable yields generally higher than 70% by moles and in a few cases even higher than 80% by moles, (2,2)-paracyclophane and its derivatives substituted in the nucleus, with a high degree of purity (above 98%) and a high productivity.

The present invention is still further elucidated by the following examples, which however are to be construed as merely illustrative and not limitative of the invention. In the examples, unless otherwise specified, all parts, percentages, and ratios are by weight.

EXAMPLE 1

(Comparative Test)

Into a 1,000 ml flask equipped with a stirrer, thermometer, and condenser, there were charged:

60 g of an aqueous solution containing 40% by weight of NaOH (0.6 moles); and 62.5 g of an aqueous solution containing 63.9% by weight of p-methylbenzyltrimethylammoniumchloride (0.2 moles).

Under continuous stirring, the solution was gradually heated to a temperature of 120° C. The soda concentration was maintained at 30% by weight. The solution was maintained at the boiling temperature over the course of 5 hours.

The resulting (2,2)-paracyclophane was separated from the reaction mass by solubilization in 300 ml of xylene. For this purpose, xylene was added to the reaction mass and the slurry was maintained at full reflux under stirring during 0.5 hours. The reaction mass was filtered at 95° C., the aqueous phase was separated from the organic solution, and this solution was repeatedly washed with water and concentrated to a small volume. The xylene solution was cooled down to 20° C. and the precipitated solid was recovered by filtration. After washing the solid with acetone and drying, there were obtained 1.08 g of a crystalline white solid (yield 5.2% by moles), having a melting point of 283°–285° C., which, on gas-chromatographic analysis, proved to be (2,2)-paracyclophane having a degree of purity of about 99.5%.

EXAMPLES 2–7

Into a 500 ml flask equipped with a stirrer, thermometer, condenser, and valves for $N_2$ flow, there were charged:

23.4 g of p-methylbenzyltrimethylammonium chloride mono-chloro substituted in the nucleus (0.1 moles);

90 g of $H_2O$;

38 g of KOH at 85% (0.575 moles);

115 g of diethylene glycol-di-methyl ether (diglyme); and a compound of the type and in the amount reported in Table 1.

Under continuous stirring, and in a $N_2$ stream, the solution was gradually heated bringing the temperature to 95° C.

The reaction mixture was maintained under these conditions over the course of 10 hours.

A further 6.6 g of KOH at 85% (0.1 moles) were then added and the reaction was completed in a further 2 hours.

The cooled raw material was diluted with 300 g of $H_2O$ and the thus-obtained solid mass was filtered.

The precipitate was treated with 250 g of n-hexane under reflux for 0.5 hours.

The reaction mass was filtered and from the resulting solution there were obtained, after removal of the solvent, a mixture of isomers of dichloro-substituted (2,2)-paracyclophane of the formula:

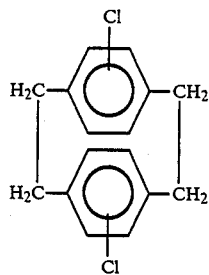

determined by NMR analysis, in an amount and with yields reported in the following table.

The purity of the dichloro substituted (2,2-paracyclophane, measured by gas-chromatography, was higher than 99%.

TABLE 1

| Example | ADDED COMPOUND | | OBTAINED PRODUCT | | |
|---|---|---|---|---|---|
| | Type | Amount in Moles | Quantity | | Yield % by moles |
| | | | g | moles | |
| 2 | p-nitro-phenol | 0.02 | 12.9 | 0.0465 | 93 |
| 3 | 2,4-dinitro-phenol | 0.02 | 12.2 | 0.044 | 88 |
| 4 | p-carboethoxy-phenol | 0.02 | 11.8 | 0.0426 | 85 |
| 5 | p-carboxy-phenol | 0.02 | 11.1 | 0.040 | 80 |
| 6 | p-hydroxy-acetophenone | 0.02 | 12.1 | 0.0435 | 87 |
| 7 | 4-nitro-alpha-naphthol | 0.02 | 11.8 | 0.0425 | 85 |

EXAMPLE 8

Into a 500 ml flask equipped with a thermometer, stirrer, condenser, and valves for $N_2$ flow, there were charged:

19.95 g of p-methylbenzyltrimethylammonium chloride (0.1 moles).
90 g of $H_2O$;
24 g of NaOH (0.6 moles);
115 g of tetraethylene glycol dimethyl ether (tetraglyme); and
2.8 g of p-nitro-phenol (0.02 moles).

Under continuous stirring and in a $N_2$ stream, the solution was gradually heated bringing the temperature to 95° C.

The reaction mixture was maintained under these conditions over the course of 10 hours.

The cooled raw material was diluted with 300 g of $H_2O$ and the obtained solid mass was filtered.

The precipitate was treated with 250 g xylene for 0.5 hours under reflux.

The reaction mass was filtered at 95° C. and the organic phase was concentrated to a low volume.

The xylene solution was cooled at 20° C. and the precipitated solid product was recovered by filtration.

After washing the solid product with acetone and after drying, there were obtained 7.8 g of a white crystalline solid product (yield 75% by moles) having a melting point of 283°–285° C. and proving, by gas-chromatographic analysis, to be (2,2)-paracyclophane with a purity of about 99.5%.

What is claimed is:

1. A process for preparing (2,2)-paracyclophane and derivatives thereof of the formula:

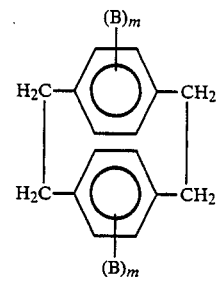

wherein B is a halogen atom, an alkyl radical, an aralkyl radical, or a halo-aralkyl radical, having up to 20 carbon atoms, and m is zero or an integer from 1 to 4, by the Hofmann elimination of p-methylbenzyltrimethylammonium hydroxide or derivatives thereof of the formula:

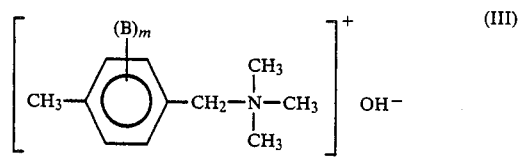

wherein B and m are the same as defined hereinabove, in an alkaline aqueous solution, characterized in that said elimination is carried out in the presence of at least a catalytic amount of an aromatic compound having the formula:

$$Y-A-(X)_n \quad (I)$$

wherein A represents an aromatic group, Y an electron donor group, X an electron acceptor, and n is an integer from 1 to 3.

2. The process according to claim 1, characterized in that in the catalyst of formula (I), A represents a phenyl or naphthyl group, Y is an OR group wherein R represents a hydrogen atom or an alkyl group having from 1 to 4 carbon atoms, and X represents a halogen atom, a nitro group, a nitrile group, a carboxyl, carboalkoxyl, carbonyl-alkyl, sulphonylalkyl group having from 1 to 6 carbon atoms in the alkyl part, or a sulphonic group.

3. The process according to claim 1 or 2, characterized in that p-methylbenzyltrimethylammonium hydroxide of formula (III) is prepared in situ from the corresponding halide by the action of the alkali metal hydroxide present in the reaction medium.

4. The process according to claim 1 or 2, characterized in that it is carried out in the presence of an aprotic organic solvent.

5. The process according to claim 4, characterized in that the aprotic organic solvent is dialkyl ether of mono- and poly-ethylene glycols having the formula:

$$R_1-O-[CH_2-CH_2O]_p-R_2 \quad (IV)$$

wherein $R_1$ and $R_2$, the same or different from each other, represent alkyl groups having from 1 to 5 carbon atoms, and p is an integer from 1 to 5.

6. The process according to claim 4, characterized in that the organic aprotic solvent is selected from the group consisting of dimethyl-sulphoxide, dimethylformamide and dimethylacetamide.

7. The process according to claim 5, characterized in that the solvent is di-ethylene-glycol-dimethyl ether.

8. The process according to claim 1 or 2, characterized in that the catalyst is selected from the group consisting of p-nitrophenol, p-cyanophenyl, p-chlorophenol, 4-nitro-alphanaphthol, p-carbomethoxyphenyl, p-carboxyphenol, 2,4-dinitrophenol, p-carboethoxyphenol, p-hydroxy acetophenone, p-hydroxybenzenesulphonic acid, and alpha-naphthol-4-sulfonic acid.

9. The process according to claim 1 or 2, characterized in that the catalyst of formula (I) is used in a molar amount ranging from 5% to 30% based on p-methylbenzyltrimethylammonium hydroxide of formula (III).

10. The process according to claim 9, characterized in that the catalyst of formula (I) is used in a molar amount ranging from 10% to 20% based on p-methylbenzyltrimethylammonium hydroxide of formula (III).

11. The process according to claim 4, characterized in that the weight ratio: organic aprotic solvent/p-methylbenzyltrimethylammonium hydroxide of formula (III) is between 2 and 50.

12. The process according to claim 11, characterized in that the weight ratio: organic aprotic solvent/p-methylbenzyltrimethylammoniun hydroxide of formula (III) is between 4 and 10.

13. The process according to claim 1 or 2, characterized in that the concentration of the aqueous solution of an alkali metal hydroxide is maintained, during the Hofmann elimination reaction, at from 15 to 35% by weight.

14. The process according to claim 1 or 2, characterized in that the molar ratio of the alkali metal hydroxide to p-methylbenzyltrimethylammonium hydroxide of formula (III) is between 1 and 10.

15. The process according to claim 1 or 2, characterized in that the Hofmann elimination is carried out at a temperature between 50° C. and 150° C. over the course of 1 to 40 hours.

16. The process according to claim 1 or 2, characterized in that the Hofmann elimination is carried out at a temperature between 70° C. and 125° C. over the course of 5 to 20 hours.

17. The process according to claim 1 or 2, characterized in that the Hofmann elimination is carried out in the presence of an inert organic solvent which is immiscible with water.

* * * * *